US006062494A

United States Patent [19]

Mills

[11] Patent Number: 6,062,494

[45] Date of Patent: May 16, 2000

[54] DRYWALL TEXTURE SPRAYER

[75] Inventor: Gregory B. Mills, Seneca, Mo.

[73] Assignee: Spraytex, Inc., Calabasas, Calif.

[21] Appl. No.: 09/140,032

[22] Filed: Aug. 26, 1998

Related U.S. Application Data

[60] Provisional application No. 60/056,377, Aug. 26, 1997.

[51] Int. Cl.[7] .......... A61M 11/02

[52] U.S. Cl. .......... 239/373; 239/318; 239/337

[58] Field of Search .......... 239/373, 337, 239/317, 318; 401/187, 188 R, 190, 118, 120

[56] References Cited

U.S. PATENT DOCUMENTS

| | | | |
|---|---|---|---|
| 1,566,325 | 12/1925 | Hansen . | |
| 2,625,433 | 1/1953 | Vose . | |
| 2,886,252 | 5/1959 | Ehrensperger . | |
| 3,236,459 | 2/1966 | McRitchie . | |
| 3,841,555 | 10/1974 | Lilja | 239/373 |
| 4,034,916 | 7/1977 | Forsberg | 239/373 |
| 4,116,382 | 9/1978 | Clerk | 239/373 |
| 4,948,054 | 8/1990 | Mills . | |
| 5,054,687 | 10/1991 | Burns et al. | 239/373 |

*Primary Examiner*—David J. Walczak
*Attorney, Agent, or Firm*—Pillsbury Madison & Sutro LLP

[57] ABSTRACT

A portable drywall texture sprayer includes a generally cylindrical tank filled with fluid drywall material, a tool connected to the tank through a set of hoses or lines, and an air supply connected to the tank. The set of hoses or lines includes a material line and a control line. The material line is connected between the tank and the tool such that there is material flow communication therebetween. The control line is connected between the tank and the tool such that there is air flow communication therebetween. An air tube is mounted within the tank and connected to the control line such that there is air flow communication therebetween. An air duct connects the air tube and the air supply such that there is air flow communication therebetween. The sprayer also includes a control orifice on the tool for controlling the air pressure within the tank. When the control orifice is covered, the air pressure within the tank increases, air is forced through the control line and the tool, and the fluid drywall material is urged through the material line and the tool, resulting in the atomization and spraying of the fluid drywall material onto the work surface. To stop the spraying of the fluid drywall material, the control orifice is uncovered. The sprayer also includes multiple mechanisms for relieving the air pressure within the tank.

15 Claims, 8 Drawing Sheets

DRYWALL TEXTURE SPRAYER

RELATED APPLICATIONS

This application claims the benefit of U.S. Provisional Application Ser. No. 60/056,377, filed Aug. 26, 1997.

FIELD OF THE INVENTION

This invention relates to drywall texture sprayers, and, in particular embodiments, to a portable drywall texture sprayer with a tool connected to a set of hoses or lines.

BACKGROUND OF THE INVENTION

Traditionally there are three general classes of drywall texture sprayers; hand-held manually powered units, air compressor powered units and motorized units which may have a mechanical mixing tank.

Hand-held units that are manually operated consist of a hand-pumped air piston, a body and a material holding tank. The user manually operates the hand pump to create a compressed air flow. The material may be supplied by gravity or by suction from the air flow. One major drawback is the awkwardness and weight of the device when held at arm's length while vigorously pumping the manual air pump. This device is similar to the hand-pumped bug sprayers. Devices of this class are limited to small patches and the like and are not practical for larger jobs. The advantage is that they can be used where there is no electricity or air supply.

Hand-held units that use compressed air are commonly referred to as hoppers. Hoppers hold a supply of fluid drywall texture. Most hoppers consist of two basic parts: the hopper and a gun-like element below the hopper that has a trigger to run the flow of material on and off. There may also be a control valve for the compressed air flow. Such texture hoppers become heavy when filled with fluid texture. The users of such hoppers commonly are covered with overspray since the hopper is held overhead when in use. A further drawback is that the supersonic air flow created as the air jet generates a vibration that separates texture into the component parts by a way of a liquefaction effect. When stratification of the material occurs, the granular material sinks to the bottom of the hopper where it packs the gun and clogs the spray orifice. Hoppers are prone to break and need repair due to mechanical elements that wear and are glued together by dry texture when the hopper is not cleaned properly. While some recent hopper sprayers have legs on them, the bulk of hand-held hoppers will not stand upright on the ground for filling without risk of falling over.

Motorized drywall texture spray units generally consist of a motorized fluid pump which feeds the fluid texture material through a hose to a remote gun for easy application and an air compressor to atomize the material at the gun. Some smaller motorized units are built into a dolly for use in elevators and highrise buildings, while the larger motorized units are built into the frames of dedicated trucks or manufactured as trailers. Some smaller motorized rigs and all of the larger units have a mixing tank or two as part of the assembly. These units allow a person to spray texture while holding a gun at arms length which is not so laborious or messy. The disadvantage of motorized texture spray devices is the complexity, size and cost.

SUMMARY OF THE DISCLOSURE

It is an object of an embodiment of the present invention to provide an improved drywall texture sprayer, which obviates for practical purposes, the above-mentioned limitations. It is an object of an embodiment of the present invention to provide a drywall texture sprayer that is inexpensive, operates on a small, portable air compressor, includes few (if any) moving parts, stands upright on the floor, and provides a spray gun or other tool to control the spraying of the drywall texture and thus allow the user to remain cleaner while using the sprayer.

According to an embodiment of the present invention, a drywall texture sprayer includes a generally cylindrical tank filled with fluid drywall material, a tool connected to the tank through a set of hoses or lines such that there is material and air flow communication therebetween, and an air supply connected to the tank and to the set of lines such that there is air flow communication therebetween. The sprayer also includes means for controlling the air pressure within the tank. When the air pressure-controlling means is used to increase the air pressure within the tank, air is forced through the set of lines and the tool, and the fluid drywall material is urged from the tank through the set of lines and the tool, such that the fluid drywall material is sprayed onto the work surface.

In particular embodiments of the present invention, the sprayer further includes an air tube mounted within the tank and connected to the set of lines such that there is air flow communication therebetween and an air duct connecting the air tube and the air supply such that there is air flow communication therebetween. In other embodiments of the present invention, the tank includes a generally cylindrical body with top and bottom ends, a sealing cap attached to the top end, and a base part attached to the bottom end. The tank also includes a pin connected to the air supply, which secures the sealing cap to the body. The body has grooves adjacent the top end thereof for relieving air pressure within the tank. The sealing cap includes a sealing ring, which abuts against the inner surface of the body such that a seal is formed between the cap and the body. The sealing cap also includes a plug for relieving excess air pressure within the tank. The sealing cap further includes a handle for attaching the cap to, and removing the cap from, the body and for carrying the tank. In still other embodiments of the present invention, the set of hoses or lines includes a material line and a control line. The material line is connected between the tank and the tool such that there is material flow communication therebetween. The control line is connected between the tank and the tool such that there is air flow communication therebetween. The control line surrounds the material line such that a coaxial line is formed. When the air pressure-controlling means is used to increase the air pressure within the tank, air is forced through the control line and the tool, and the fluid drywall material is urged through the material line and the tool, such that the fluid drywall material is sprayed onto the work surface. In yet other embodiments of the present invention, the means for controlling the air pressure within the tank is a control orifice on the tool, and the air pressure within the tank is increased by covering the control orifice on the tool.

In accordance with another embodiment of the present invention, a drywall texture sprayer includes a generally cylindrical tank filled with fluid drywall material, a tool connected to the tank through a set of conduit hoses or lines, and an air supply connected to the tank. The set of conduit hoses or lines includes a material line and a control line. The material line is connected between the tank and the tool such that there is material flow communication therebetween. The control line is connected between the tank and the tool such that there is air flow communication therebetween. An air tube is mounted within the tank and connected to the control line such that there is air flow communication therebetween. An air duct connects the air tube and the air supply such that there is air flow communication therebetween. The sprayer also includes a control orifice on the tool for controlling the air pressure within the tank. When the control orifice is covered, the air pressure within the tank increases, air is forced through the control line and the tool, and the fluid drywall material is urged from the tank through the material line and the tool, such that the fluid drywall material is sprayed onto the work surface.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
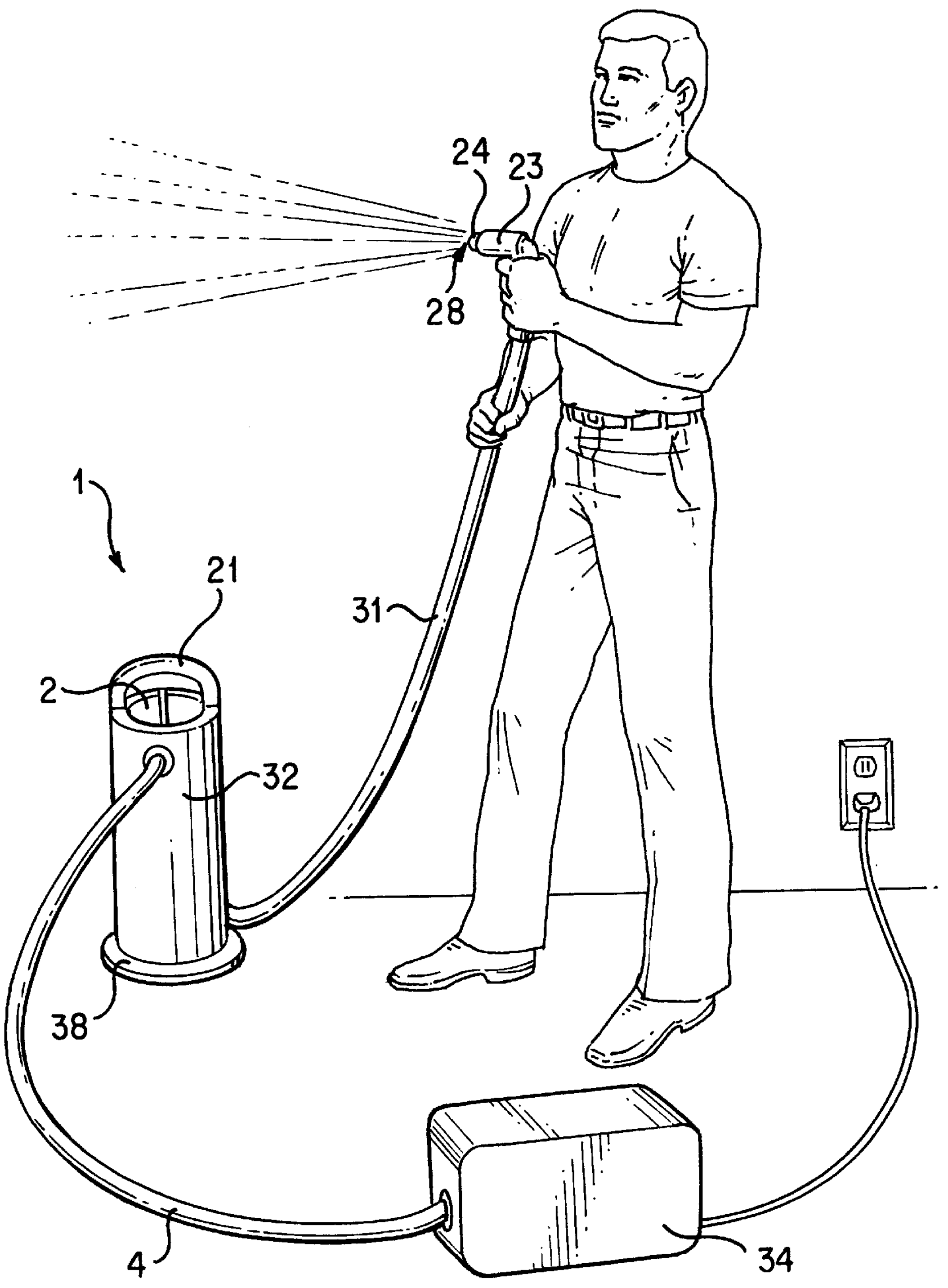
FIG. 1 is a perspective view of a drywall texture sprayer in accordance with an embodiment of the present invention.

As shown in the drawings for purposes of illustration, the invention is embodied in a drywall texture sprayer. In preferred embodiments of the present invention, the drywall texture sprayer is used to apply drywall texture or fluid drywall material onto a work surface. However, it will be recognized that further embodiments of the invention may be used to apply other materials onto work surfaces, such as paint, water, or the like.

FIG. 1 illustrates a perspective view of a drywall texture sprayer in accordance with an embodiment of the present invention. The sprayer includes a generally cylindrical tank 1 filled with drywall texture or fluid drywall material 11, a compressed air supply 34 connected to the tank 1 through an air supply hose 4, and a spray tool 23 connected to the tank 1 through a set of hoses or lines 31. In preferred embodiments, an air supply 34 having ¾ horsepower is utilized to operate the sprayer. Air compressors up to 1.25 horsepower should be adjusted downwards or excesss air pressure bled off.

Figure 2:
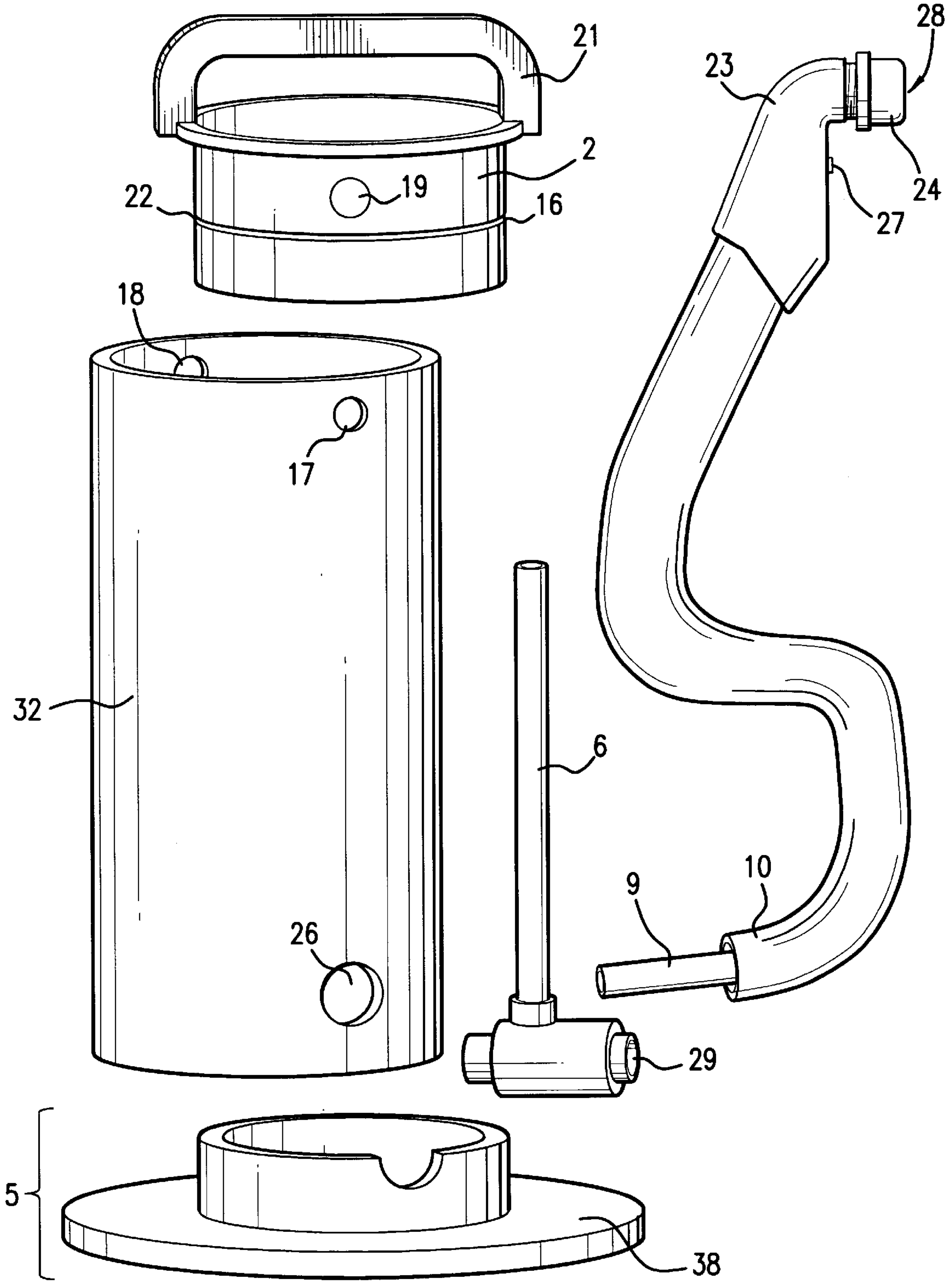
FIG. 2 is a perspective view of parts of the drywall texture sprayer in accordance with an embodiment of the present invention.
Figure 3:
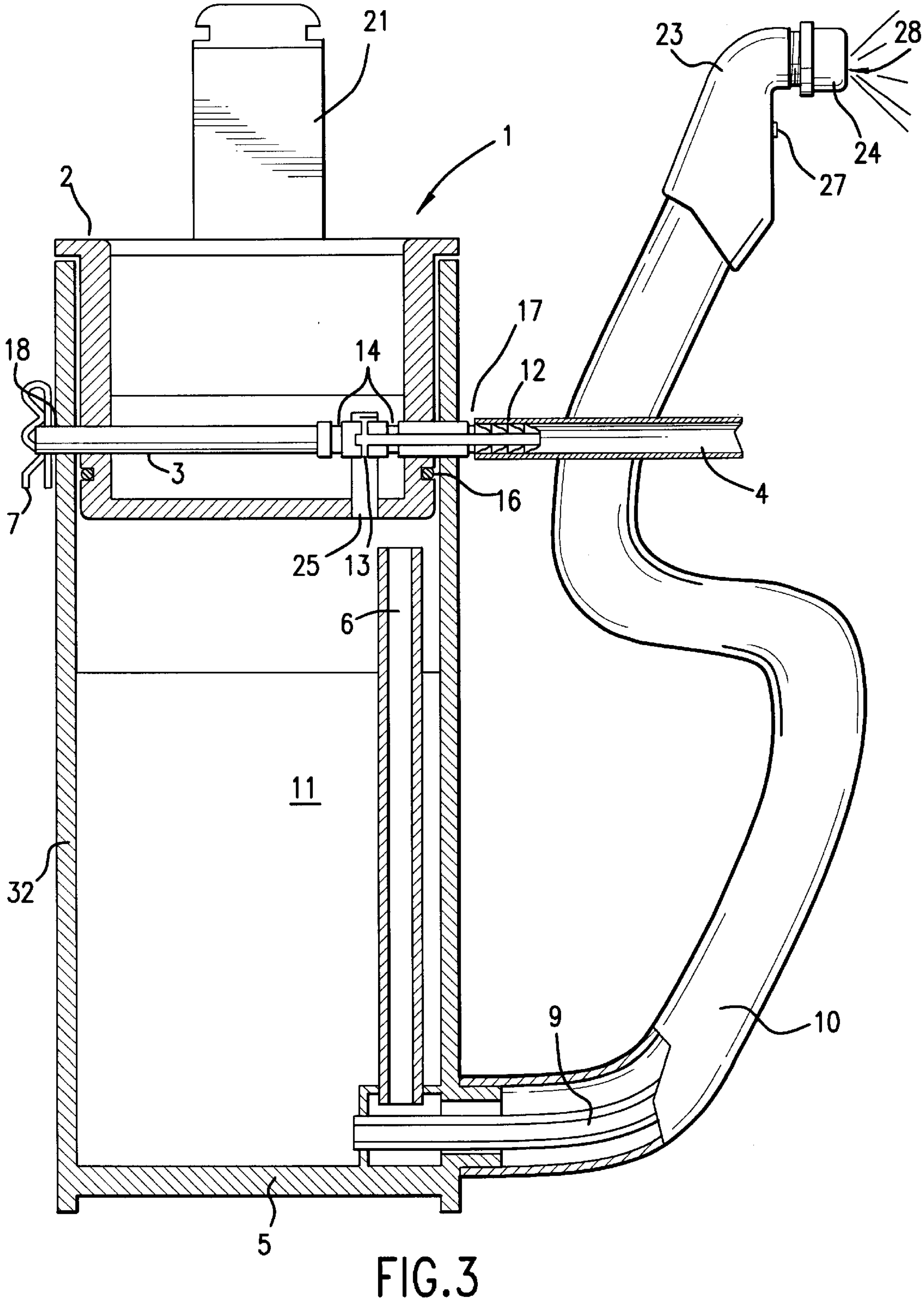
FIG. 3 is a partial cross-sectional view of the drywall texture sprayer in accordance with an embodiment of the present invention.
Figure 4:
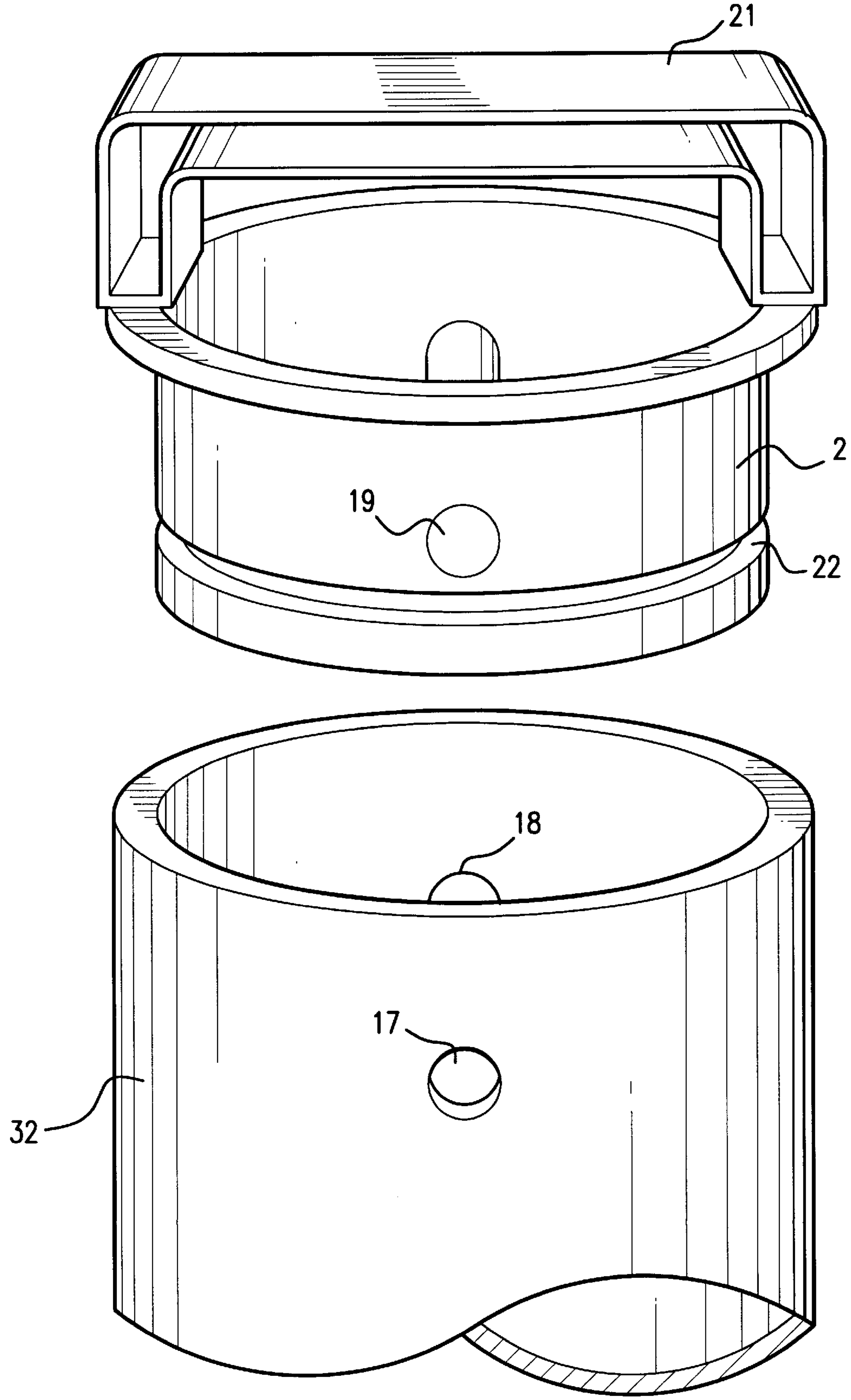
FIG. 4 is an exploded perspective view of a sealing cap and a tank body in accordance with an embodiment of the present invention.

In the embodiment illustrated in FIGS. 2 and 3, the set of lines 31 connected between the tank 1 and the tool 23 includes a material line 9 and an air or control line 10. The material line 9 supplies the fluid drywall material 11 from the tank 1 to the tool 23. The control line 10 supplies air between the tank 1 and the tool 23. Air pressure within the tank 1 is also controlled using the control line 10.

In preferred embodiments, the material line 9 and the control line 10 are made from a flexible material to withstand the air pressure applied by the air supply 34 as well as to facilitate manipulation of the tool 23 by the user. In one embodiment, the material line 9 and the control line 10 are made of rubber or synthetic rubber-like material. However, in alternative embodiments, the material line 9 and the control line 10 may be made of other materials, such as plastic, metal, composites, or the like.

In the embodiment illustrated in FIGS. 2 and 3, the control line 10 surrounds the material line 9 such that a coaxial line 31 is formed. One end of the coaxial line 31 is attached to a hose or line fitting part 29 on the tank 1, and the other end of the coaxial line 31 is attached to the tool 23. The coaxial line 31 is attached to the line fitting part 29 and the tool 23 using glue, fittings, fasteners, or the like. In alternative embodiments, the material line 9 and the control line 10 may be two separate lines, each of which is individually attached to the tank 1 and the tool 23.

Figure 8A:
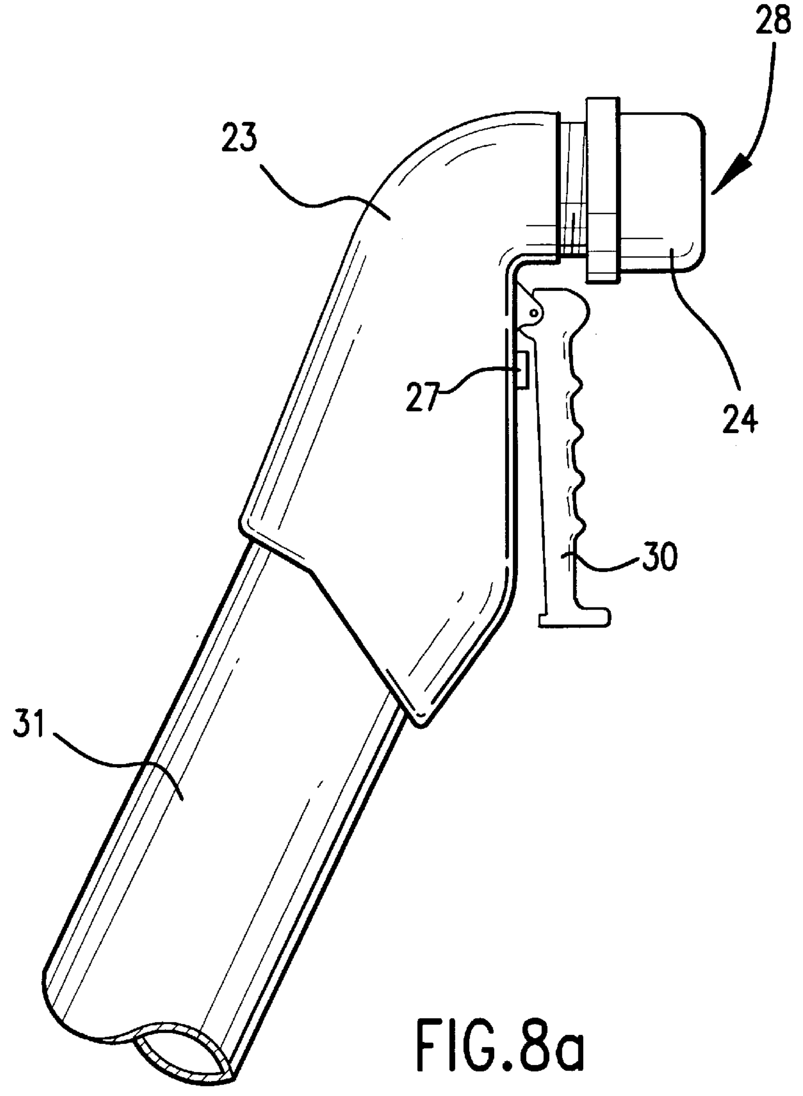
FIG. 8*a* is an exploded perspective view of a spray gun in accordance with an embodiment of the present invention.
Figure 8B:
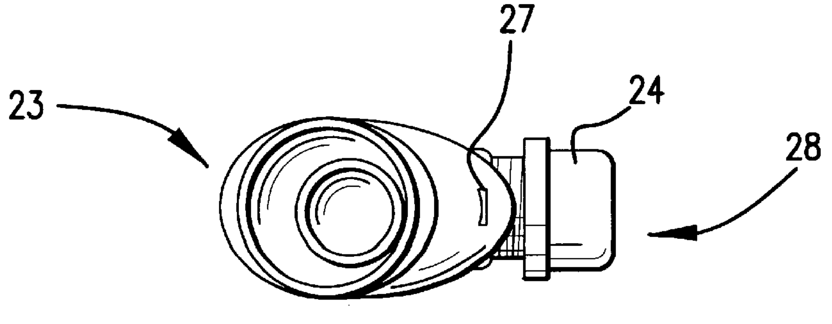
FIG. 8*b* is an exploded bottom plan view of the spray gun shown in FIG. 8*a*.
Figure 8C:
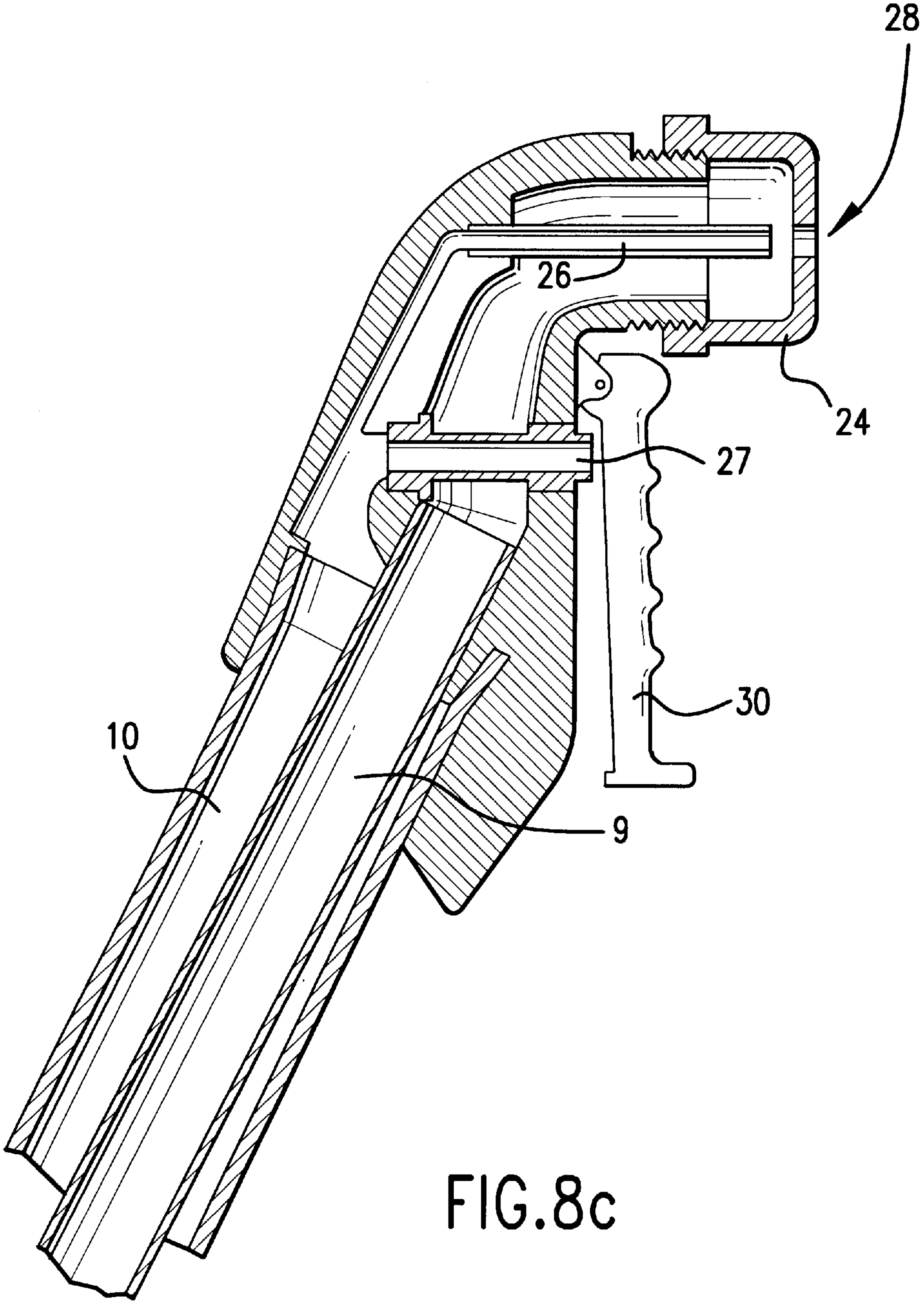
FIG. 8*c* is a cross-sectional view of the spray gun shown in FIG. 8*a*.

In the embodiment illustrated in FIGS. 1–3 and 8*a*–8*c*, the spray tool 23 is a spray gun 23. In one embodiment, the gun 23 is made of metal. However, in alternative embodiments, the gun 23 is made of other materials, such as plastic, ceramic, composites, or the like. In preferred embodiments, the gun 23 is ergonomically adapted for operation by both left-handed and right-handed users. The tip of the gun 23 has a spray cap or nozzle 24 with a spray orifice 28. As shown in FIGS. 8*a*–8*c*, the spray nozzle 24 has threads which mate with threads on the tip of the gun 23, such that the nozzle 24 is secured to the tip of the gun 23 and is moved linearly along the tip of the gun 23 as the nozzle 24 is rotated about the tip of the gun 23. The spray nozzle 24 may thus be screwed on tighter or looser to adjust the manner in which drywall texture 11 is sprayed from the gun 23. Additionally, the spray nozzle 24 may be removed and replaced by another spray nozzle 24 with a spray orifice 28 which has a different diameter. In alternative embodiments, a rotatable disk with a certain number of spray orifices 28 which have different diameters may be mounted on the spray nozzle 24. In further alternative embodiments, a spray nozzle 24 that may be rotatably adjusted to provide spray orifices 28 which have a range of different diameters may be used.

The gun 23 is attached to the set of lines 31 using glue, fittings, fasteners, or the like. As shown in FIG. 8*c*, the material line 9 extends from the bottom of the gun and supplies fluid drywall material 11 to the spray orifice 28. The control line 10 extends from the bottom of the gun 23 to a "y"-shaped juncture. One leg of the juncture leads to a control orifice 27. In the illustrated embodiment, the control orifice 27 provides the means for controlling the air pressure within the tank 1. As described below, the control orifice 27 is covered and uncovered to control the air pressure within the tank 1 and the spraying of fluid drywall material 11 from the gun 23. In alternative embodiments, the means for controlling the air pressure within the tank 1 may be a control orifice on the control line 10 or on the tank 1, an air release valve on the tank 1, or the like. In the embodiment illustrated in FIGS. 8*a*–8*c*, the gun 23 has a trigger 30, which the user may depress to cover the control orifice 27. In alternative embodiments, the trigger 30 may be omitted, and the user may cover the control orifice 27 with his finger. As illustrated in FIG. 8*c*, the other leg of the juncture leads to an air orifice 26, which is located behind the spray orifice 28. The diameter of the air orifice 26 is smaller than the diameter of the spray orifice 28. The air orifice 26 thus creates supersonic air flow behind the spray orifice 28, resulting in the atomization and spraying of the fluid drywall material 11 onto the work surface. In alternative embodiments, a one-way valve may be included at the air orifice 26 to prevent the back flow of fluid drywall material 11 into the control line 10.

In the embodiment illustrated in FIGS. 1–3, the tank 1 includes a sealing cap 2, a generally cylindrical tank body 32, and a base part 5. In preferred embodiments, the tank body 32 is made of a material and has a wall thickness that are sufficient to withstand the air pressure applied by the air supply 34. In one embodiment, the tank body 32 is made of metal. However, in alternative embodiments, the tank body 32 may be made of other materials, such as plastic, ceramic, composites, or the like. The outer surface of the tank body 32 may be decorated to conform to the brand name and style of the company that sells the sprayer. The outer surface of the tank body 32 may also be covered with detailed operation and safety instructions for the sprayer.

In preferred embodiments, the sealing cap 2 also is made of a material and has a thickness that are sufficient to withstand the air pressure applied by the air supply 34. In one embodiment, the cap 2 is made of metal. However, in alternative embodiments, the cap 2 may be made of other materials, such as plastic, ceramic, composites, or the like.

In the embodiment illustrated in FIGS. 1–3 and 5, the sealing cap 2 attaches to and detaches from the top end of the tank body 32. In one embodiment, the cap 2 has threads which mate with threads along the inner surface of the tank body 32 to attach the cap 2 to the tank body 32. The user may thus twist the cap 2 to attach the cap 2 to, and to remove the cap 2 from, the tank body 32. In alternative embodiments, the cap 2 may be attached to and detached from the tank body 32 by pushing down and pulling up the cap 2. In further alternative embodiments, the cap 2 may be attached to the tank body 32 using fasteners or the like.

In the illustrated embodiment, the cap 2 has a handle 21, which may be used to attach the cap 2 to, and to remove the cap 2 from, the tank body 32, as well as to carry the tank 1. The cap 2 also has a sealing ring 16, which fits within a circumferential groove 22 in the cap 2. In one embodiment, the sealing ring 16 is made of rubber or synthetic rubber-like material. However, in alternative embodiments, the sealing ring 16 may be made of other materials, such as metal, plastic, composites, or the like. In preferred embodiments, when the cap 2 is attached to the tank body 32, the sealing ring 16 abuts against the inner surface of the tank body 32 such that an air tight seal is formed between the cap 2 and the tank body 32.

In the embodiment illustrated in FIGS. 2–5 and 7*a*–7*c*, the sealing cap 2 is secured to the tank body 32 using an air supply pin 3. In one embodiment, the pin 3 is made of metal. However, in alternative embodiments, the pin 3 may be made of other materials, such as plastic, ceramic, composites, or the like. In the illustrated embodiment, the pin 3 is inserted through holes 17 and 18 in the tank body 32 and a hole 19 in the cap 2. One end of the pin 3 has a groove 8 for receiving a pin clip 7, which secures the pin 3 to the cap 2 and the tank body 32. The pin 3 thus holds the cap 2 in place and prevents the cap 2 from being blown off the tank body 32 due to excessive air pressure within the tank 1. Additionally, the tank 1 cannot be pressurized unless the pin 3 is in place. The other end of the pin 3 has hose or line barb 12 for easy attachment and removal of the air supply hose 4, which is connected to the air supply 34. Air is provided from the air supply 34 through the air supply hose 4, and the air is directed to an air passage 13 in the pin 3. The air passage 13 in the pin 3 is connected to an air duct 25 in the sealing cap 2, which leads to the interior of the tank 1. Thus, there is air flow communication between the air supply 34 and the interior of the tank 1. The pin 3 also has grooves 14 on each side of the air passage 13 for receiving O-rings 15. In alternative embodiments, the air supply pin 3 may be omitted. In such alternative embodiments, the cap 2 may be secured to the tank body 32 using fasteners or the like, and the air supply 34 may be connected in air flow communication with the interior of the tank 1 through an air duct or series of air tubes and ducts.

In the embodiment illustrated in FIGS. 1–3, the base part 5 is attached to the bottom end of the tank body 32. In one embodiment, the base part 5 is made of metal and is molded with the bottom end of the tank body 32. However, in alternative embodiments, the base part 5 may be made of other materials, such as plastic, ceramic, composites, or the like. In further alternative embodiments, the base part 5 may be attached to the bottom end of the tank body 32 using materials, such as glue, fasteners, or the like, or using processes, such as welding or the like. In preferred embodiments, an airtight seal is thus formed between the base part 5 and the tank body 32. The base part 5 also has a bottom plate 38 for placing and stabilizing the tank 1 on a floor surface.

In the embodiment illustrated in FIGS. 2 and 3, an air or stand tube 6 is mounted within the tank 1 and is supported by the base part 5. In one embodiment, the air tube 6 is made of metal. However, in alternative embodiments, the air tube 6 is made of other materials, such as plastic, ceramic, composites, or the like. In the illustrated embodiment, the air tube 6 is a separate part that is mounted within the tank 1. However, in alternative embodiments, the air tube 6 may be molded as a part of the tank 1. In the illustrated embodiment, when the air tube 6 is installed in the tank 1, the upper end of the air tube 6 is located below the bottom of the sealing cap 2. In alternative embodiments, the air tube 6 may have a bend, such as a 180 degree bend, to prevent fluid drywall material 11 from flowing down the air tube 6. As shown in FIGS. 2 and 3, a hose or line fitting part 29 is attached to the lower end of the air tube 6. The line fitting part 29 is inserted through a line fitting hole 26 in the tank body 32, and the set of lines 31, which includes the material line 9 and the control line, attaches to the line fitting part 29. In alternative embodiments, the line fitting part 29 may have two connections for attaching separate material and control lines 9 and 10.

Figure 5:
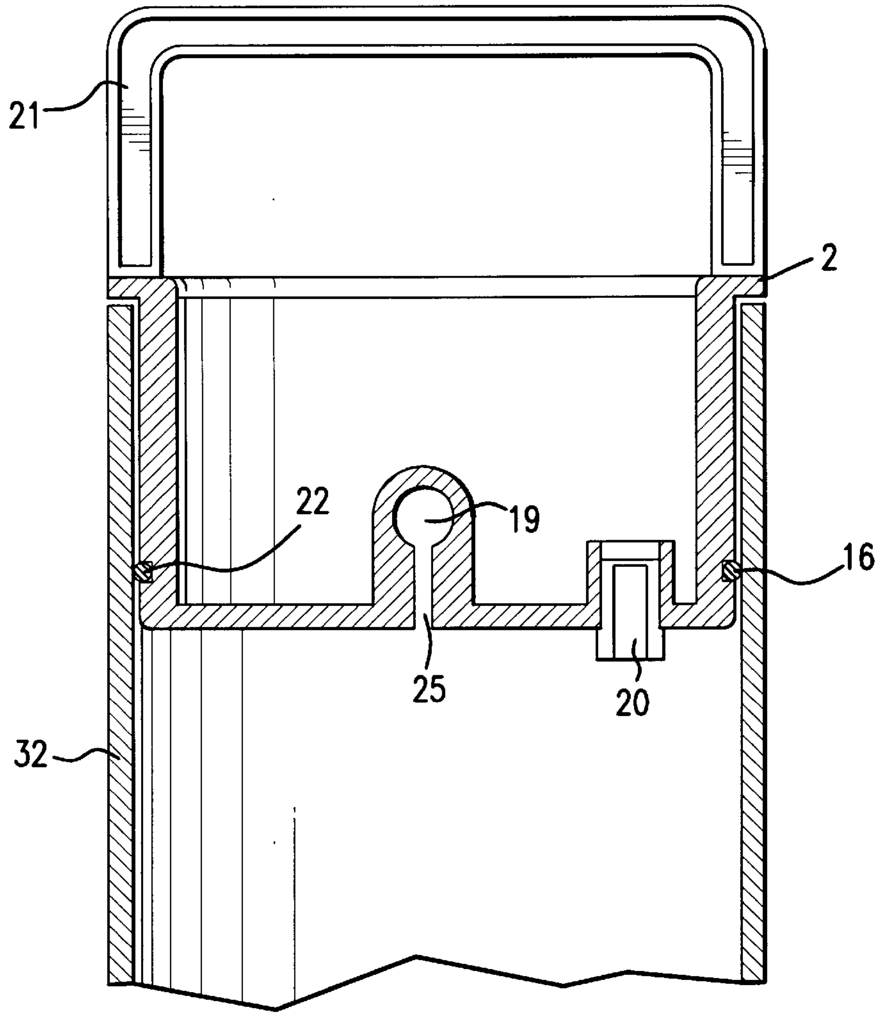
FIG. 5 is a partial cross-sectional view of the sealing cap attached to the tank body in accordance with an embodiment of the present invention.
Figure 6:
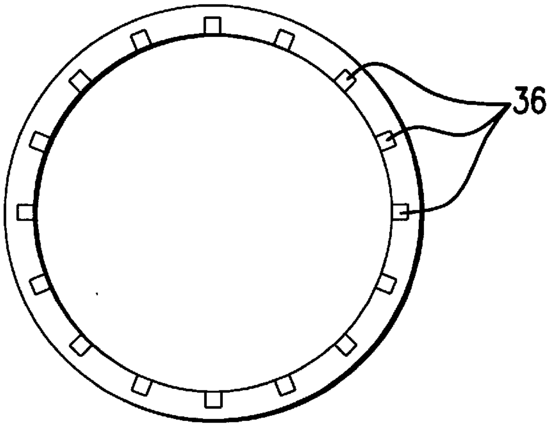
FIG. 6 is an exploded top plan view of grooves in the tank body in accordance with an embodiment of the present invention.
Figure 7A:
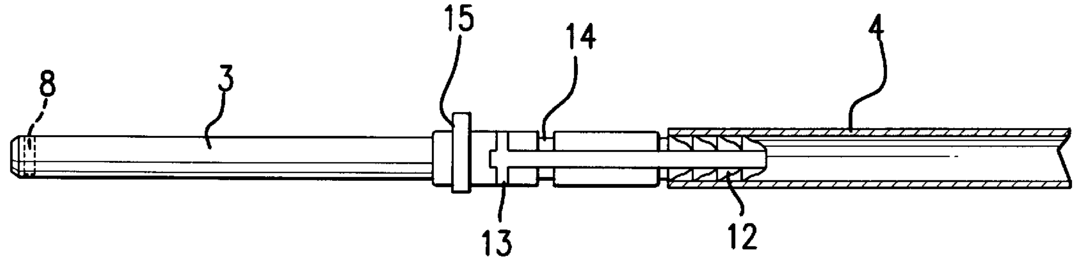
FIG. 7*a* is an exploded perspective view of an air supply pin in accordance with an embodiment of the present invention.
Figure 7B:
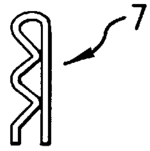
FIG. 7*b* is an exploded perspective view of a pin clip for use with the air supply pin shown in FIG. 7*a*.
Figure 7C:
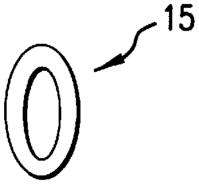
FIG. 7*c* is an exploded perspective view of an O-ring for use with the air supply pin shown in FIG. 7*a*.

In preferred embodiments, the sprayer has multiple pressure relief mechanisms to prevent explosive depressurization of the tank 1. As illustrated in FIG. 6, the inner surface of the tank body 32 has pressure relief grooves 36 adjacent the top end of the tank body 32. The grooves 36 prevent pressurization of the tank 1 when the cap 2 is not sealed properly. The grooves 36 also allow air within the tank 1 to be released before the cap 2 could be or is blown off due to excessive pressure within the tank 1. In alternative embodiments, the grooves 36 may be omitted. In preferred embodiments, the sprayer also has an air pressure limiting and release valve (not shown). In one embodiment, the air pressure limiting and release valve is located at the hose barb end 12 of the pin 3. In alternative embodiments, the air pressure limiting and release valve may be located at the connection between the air supply hose 4 and the air supply 34. In further alternative embodiments, the air pressure limiting and release valve may be omitted. As illustrated in FIG. 5, the cap 2 has a plug 20, which may be blown out in the event of excessive pressure within the tank 1. In alternative embodiments, the plug 20 may be omitted.

In yet another embodiment, the control line 10 and the material line 9 are in a parallel allignment. A cross section of the binary hose would be similar to a figure "8." Alternatively, the hoses could be loose. The control line 10 interconnects with the spray gun 23 by way of a hose barb or compression fitting and communicates with the control orifice 27 and the air orifice 26.

To utilize the sprayer, the user removes the sealing cap 2 and fills the tank 1 with fluid drywall material 11 to a level below the upper end of the air tube 6. The user replaces the cap 2 and attaches the air supply 34 to the air supply pin 3 on the tank 1 through the air supply hose 4. Air flows through the air passage 13 in the pin 3 and the air duct 25 in the cap 2 into the interior of the tank 1. From the interior of the tank 1, the air flows through the air tube 6, the control line 10, and out through the control orifice 27 on the spray gun 23. In this state, the air pressure within the tank 1 is slightly elevated due to the air flow. When the user wants to apply the fluid drywall material 11 onto the work surface, he points the gun 23 at the work surface and restricts the flow of air out of the sprayer by covering the control orifice 27. The air pressure within the tank 1 increases, thus forcing the air to flow out of the sprayer through the air orifice 26 and the spray orifice 28. At the same time, pressure upon the fluid drywall material 11 within the tank 1 urges the fluid drywall material 11 from the tank 1, through the material line 9 and the spray gun 23, and out through the spray orifice 28 onto the work surface. The flow of the air and the fluid drywall material 11 through the spray orifice 28 results in the atomization and spraying of the fluid drywall material 11 onto the work surface. When the user wants to stop spraying the fluid drywall material 11 onto the work surface, the user uncovers the control orifice on the gun 23. A decrease in the air pressure within the tank 1 thus results, and the flow of the fluid drywall material 11 to the gun 23 stops.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. An apparatus for spraying fluid drywall material onto a work surface, the apparatus comprising:

a generally cylindrical tank adapted to be filled with the fluid drywall material;

a spray tool configured to direct the fluid drywall material on to said work surface;

conduit means connected between the tank and the tool such that there is material and air flow communication therebetween;

an air supply connected to the tank and to the conduit means such that there is air flow communication therebetween; and means for controlling the air pressure within the tank;

wherein when the air pressure-controlling means is closed to increase the air pressure within the tank, air is forced through the conduit means and the spray tool, and the fluid drywall material is urged from the tank through the conduit means and the spray tool, such that the fluid drywall material is sprayed onto the work surface, and when the air pressure-controlling means is opened to decrease the air pressure within the tank, spraying of the fluid drywall material onto the work surface is stopped.

2. The apparatus of claim 1, wherein the apparatus further comprises:

an air tube mounted within the tank and connected to the conduit means such that there is air flow communication therebetween; and an air duct connecting the air tube and the air supply such that there is air flow communication therebetween.

3. The apparatus of claim 1, wherein the tank comprises:

a generally cylindrical body with top and bottom ends;

a sealing cap attached to the top end; and a base attached to the bottom end.

4. The apparatus of claim 3, wherein the tank further comprises a pin connected to the air supply, wherein the pin secures the sealing cap to the body.

5. The apparatus of claim 3, wherein the body further comprises grooves adjacent the top end thereof for relieving air pressure within the tank when the cap is not properly in place.

6. The apparatus of claim 3, wherein the sealing cap further comprises a sealing ring, wherein when the sealing cap is attached to the body, the sealing ring abuts against the inner surface of the body such that a seal is formed between the cap and the body.

7. The apparatus of claim 3, wherein the sealing cap further comprises a plug for relieving excess air pressure within the tank.

8. The apparatus of claim 3, wherein the sealing cap further comprises a handle for attaching the cap to, and removing the cap from, the body and for carrying the tank.

9. The apparatus of claim 1, wherein the conduit means comprises:

a material line connected between the tank and the spray tool such that there is material flow communication therebetween; and a control line connected between the tank and the spray tool such that there is air flow communication therebetween.

10. The apparatus of claim 9, wherein the control line surrounds the material line such that a coaxial line is formed.

11. The apparatus of claim 9, wherein the material line is made from a flexible material.

12. The apparatus of claim 9, wherein the control line is made from a flexible material.

13. The apparatus of claim 1, wherein the means for controlling the air pressure within the tank is a control orifice on the spray tool, and further wherein the air pressure within the tank is increased by covering the control orifice on the spray tool.

14. The apparatus of claim 1, wherein the spray tool is a spray gun.

15. An apparatus for spraying fluid drywall material onto a work surface, the apparatus comprising:

a generally cylindrical tank adapted to be filled with the fluid drywall material;

a spray tool;

a material line connected between the tank and the spray tool such that there is material flow communication therebetween;

a control line connected between the tank and the spray tool such that there is air flow communication therebetween;

an air tube mounted within the tank and connected to the control line such that there is air flow communication therebetween;

an air supply connected to the tank;

an air duct connecting the air tube and the air supply such that there is air flow communication therebetween; and a control orifice on the spray tool for controlling the air pressure within the tank;

wherein when the control orifice is covered, the air pressure within the tank increases, air is forced through the control line and the spray tool, and the fluid drywall material is urged from the tank through the material line and the spray tool, such that the fluid drywall material is sprayed onto the work surface.

* * * * *